United States Patent [19]

Hille et al.

[11] Patent Number: 5,700,480
[45] Date of Patent: Dec. 23, 1997

[54] TRANSDERMAL THERAPEUTIC SYSTEM COMPRISING GALANTHAMINE AS ACTIVE COMPONENT

[75] Inventors: Thomas Hille, Neuwied; Lothar Deurer, Koblenz, both of Germany

[73] Assignee: LTS Lohman Therapie-Systeme GmbH & Co. KG, Neuwied, Germany

[21] Appl. No.: 495,609

[22] PCT Filed: Jan. 10, 1994

[86] PCT No.: PCT/EP94/00054

§ 371 Date: Sep. 29, 1995

§ 102(e) Date: Sep. 29, 1995

[87] PCT Pub. No.: WO94/16707

PCT Pub. Date: Aug. 4, 1994

[30] Foreign Application Priority Data

Jan. 23, 1993 [DE] Germany ............... P 43 01 783.5

[51] Int. Cl.$^6$ .................. A61F 13/02; A61L 15/16; A61K 9/14
[52] U.S. Cl. .......................... 424/448; 424/449
[58] Field of Search ................... 424/448, 449, 424/487

[56] References Cited

U.S. PATENT DOCUMENTS 4,663,318  5/1987  Davis ..................... 514/215
5,089,267  2/1992  Hille et al. ............... 424/449

FOREIGN PATENT DOCUMENTS 4 010 079  10/1991  Germany.

*Primary Examiner*—Thurman K. Page
*Assistant Examiner*—Kathryne E. Shelborne
*Attorney, Agent, or Firm*—Wenderoth, Lind & Ponack

[57] ABSTRACT

A transdermal therapeutic system (TTS) for the administration of galanthamine to the skin each system having a backing layer which is impermeable to active substances and a pressure sensitive adhesive reservoir layer, wherein the reservoir layer comprises 40–80% wt. polymeric material selected from the group consisting of polyacrylates, 0.1–30%-wt. plasticizers, and 0.1–30%-wt. galanthamine base or one of its pharmaceutically acceptable salts.

9 Claims, No Drawings

TRANSDERMAL THERAPEUTIC SYSTEM COMPRISING GALANTHAMINE AS ACTIVE COMPONENT

The present invention relates to a transdermal therapeutic system (TTS) which comprises as active component galanthamine (4a,5,9,10,11,12-hexahydro-3-methoxy-11-methyl-6H-benzofuro (3a,3,2-ef) (2) benzazepin-6-ol).

BACKGROUND OF THE INVENTION

Owing to its pharmacological properties galanthamine belongs to the group of reversibly acting cholinesterase inhibitors. The effects are similar to those of physostigmine and neostigmine, however, it has specific properties. The therapeutic range of galanthamine is three to six times broader since it is not as toxic as physostigmine or neostigmine.

This advantage compensates for the slightly lower cholinesterase inhibiting-action, relative to the dosage.

The major fields of application of galanthamine are the treatment of the narrow-angle glaucoma and the use as antidote after curare applications. The use of galanthamine in the treatment of the Alzheimer's disease is in an experimental stage.

Lately, galanthamine has been used in the treatment of alcohol dependence (Opitz, K., DE 40 10 079).

Both the therapy of the Alzheimer's disease and that of alcohol dependence require long-acting drug forms taking into account the particular circumstances of the respective disease. Complicated therapeutic plans or prolonged infusions are unsuitable for obvious reasons.

On the contrary, a TTS is the drug form of choice; nevertheless, until today, it has not been possible to succeed in bringing the necessary amount of galanthamine to absorption transdermally.

DESCRIPTION OF THE INVENTION

Accordingly, it is the object of the present invention to provide galanthamine or one of its pharmaceutically acceptable salts in the form of a transdermal therapeutic system which releases galanthamine or its pharmaceutically acceptable salt over a period of at least 24 hours in a controlled manner and ensures that the galanthamine does not noticeably decompose during storage of the prefabricated transdermal therapeutic system and makes sure that the galanthamine penetrates through human skin to the required extent in vivo.

With the present invention this object is achieved in a surprising manner by a transdermal therapeutic system.

This solution is remarkable all the more since the structure of galanthamine is very similar to that of the opiates. Opiates are considered to be a substance class which only insufficiently penetrates human skin.

Without the intention to limit the present invention, the hydrobromide and hydrochloride of galanthamine are to be understood as the preferred pharmaceutically acceptable salts of galanthamine.

Advantageous embodiments of the present invention are further described.

The backing layer which is impermeable to active substances may consist of flexible and inflexible material. Substances suitable for the production include polymer films or foils, such as an aluminum foil, which may be used alone or coated with a polymeric substrate. Textile fabrics may also be used, provided that the components of the reservoir owing to their physical nature may not pass through. According to a preferred embodiment the backing layer is a composite of an aluminized sheet.

The reservoir layer consists of a polymer matrix and the active substance, with the polymer matrix ensuring the cohesion of the system. The polymer matrix consists of a base polymer and, optionally, conventional additives. The choice of the base polymer depends on the chemical and physical properties of the galanthamine. Examples of such polymers include rubber, rubber-like synthetic homopolymers, copolymers or block polymers, polyacrylates and the copolymers thereof, polyurethanes and silicones. In principle, all polymers are suitable which may be used in the production of pressure sensitive adhesives and which are physiologically acceptable. Particularly preferred ones are those consisting of block copolymers based on styrene and 1,3-dienes, polyisobutylenes, silicones and polymers based on acrylate and/or methacrylate.

Among the block copolymers based on styrene and 1,3-dienes, linear styrene-isoprene or styrene-butadiene-block copolymers are particularly used.

Preferred polymers based on acrylate include self-crosslinking acrylate copolymers of 2-ethyl hexyl acrylate, vinyl acetate, and acrylic acid with titanium chelate esters or non-self-crosslinking acrylate copolymers without titanium chelate esters.

Suitable polymers which are added to the basic polymer include polymethacrylates and polyvinyls.

Preferred methacrylates include copolymers based on dimethylaminoethyl methacrylates and neutral methacrylic esters. Polyvinyl pyrrolidones and polyvinyl alcohols are preferably used as polyvinyls.

The selection of the plasticizer depends on the polymer. Particularly suitable are higher alcohols, such as dodecanol, undecanol, octanol, oleyl alcohol and 2-octyl dodecanol, esters of carboxylic acids, wherein the alcohol component may also be a polyethoxylated alcohol, diesters of dicarboxylic acids, e.g., di-n-butyladipate, as well as triglycerides, in particular medium-chain triglycerides of the caprylic/capric acids of coconut oil. Additional examples of a suitable plasticizer include polyfunctional alcohols, e.g. glycerol and 1,2-propanediol and others, these may be etherified by polyethylene glycols.

Suitable penetration enhancers include all carboxylic acids which are physiologically acceptable. Particularly suitable are octanoic acid, laevulinic acid, undecenoic acid, oleic acid, as well as stearic acid and their isomers.

The nature of the conventional additives depends on the polymer used: According to their function they may be classified, e.g., into tackifiers, stabilizers, carriers, and fillers. The suitable physiologically acceptable substances are known to those skilled in the art.

The self-tackiness of the reservoir layer is strong enough to ensure permanent contact to the skin.

The removable protective layer, which is in contact with the reservoir layer and is removed prior to use, for example, consists of the same materials as those used for the manufacture of the reservoir layer, provided that they are rendered removable, e.g., by a silicone treatment. Other removable protective layers, for example, are polytetrafluoroethylene, treated paper, cellophane, polyvinyl chloride, and the like. If the laminate according to the present invention is cut into sizes (patches) corresponding to the therapeutic purpose prior to applying the protective layer, the formats of the protective layer then to be applied may have a projecting end, facilitating its removal from the patch.

The transdermal therapeutic system according to the present invention is manufactured by homogeneously mixing the active substance together with the components of the pressure sensitive adhesive reservoir layer, optionally in solution, and spreading it onto the backing layer which is impermeable to the active substance, followed by removal of the solvent(s), if necessary. Subsequently, the adhesive layer is provided with an adequate protective layer.

In principle the reverse is also possible, i.e., that the adhesive solution is spread on the protective layer. In this case too, the solvents are removed and the backing layer is applied.

The invention will be illustrated by the following examples:

EXAMPLE 1

10.0 g octanoic acid and 10.0 g isopropyl myristate are mixed under stirring. Subsequently, 10.0 g galanthamine is introduced; stirring is continued until the solid is completely dissolved (approximately 30 min.; visual control).

Then, 130.0 g of a self-crosslinking acrylate copolymer of 2-ethyl hexyl acrylate, vinyl acetate, and acrylic acid (46%) in a mixed solvent (ethyl acetate:heptane:isopropanol-:toluene:acetylacetone 37:26:26:4:1) are added under stirring, followed by homogenization. Afterwards 10 g of a methacrylate copolymer based on dimethylamino methacrylate and neutral methacrylic esters are additionally sprinkled into the mixture under stirring, and stirring is continued at room temperature for 3 hours. The evaporation loss is compensated.

150 g 52.8% (w/w) active substance-containing adhesive solution result which is spread on an aluminized and siliconized polyethylene sheet by means of a 350 μm coating knife. After the solvents have been removed by drying for 30 min. up to 60° C., the adhesive film is covered with a polyester sheet (15 μm). An area of 16 cm² is punched by means of a suitable cutting tool and the edges are separated off. The release relating to both this and the other examples is listed in the table; the list indicates both the controlled release into a physiological saline and through excized rodent skin.

All further examples are carried out in accordance with the procedure of Example 1. The liquid components are always mixed first, then the galanthamine base is sprinkled into the mixture. After dissolution, the adhesive solution is added. The following table indicates the formulation components after drying.

| Example | Galan-thamine | Polyacrylate | Poly-methacrylate | Plasticizer | Penetration enhancer | Liberation [mg/16 cm² × 24 h] | Penetration [mg/16 cm² × 24 h] |
|---|---|---|---|---|---|---|---|
| 1 | 10% | acidic PA 60% | 10% | isopryl myristate 10% | octanoic acid 10% | 20.3 | 1.0 |
| 2 | 10% | acidic PA 55% | 15% | isopropyl myristate 10% | octanoic acid 10% | 20.3 | 1.0 |
| 3 | 10% | acidic PA 55% | 10% | isopropyl myristate 15% | octanoic acid 10% | 20.4 | 0.95 |
| 4 | 10% | neutral PA 59% | 15% | oleyl alcohol 5% | octanoic acid 10% pantothenyl alcohol 1% | 20.6 | 1.05 |
| 5 | 10% | neutral PA 59% | 15% | isopropyl myristate 10% | octanoic acid 10% pantothenyl alcohol 1% | 20.5 | 1.05 |
| 6 | 10% | neutral PA 59% | 15% | oleyl alcohol 5% | octanoic acid 10% pantothenyl alcohol 1% | 18 | 0.95 |
| 7 | as in 6 | as in 6 as in 6 | as in 6 | as in 6 | oleic acid 10% pantothenyl alcohol 1% | 18.5 | 1.05 |
| 8 | as in 6 | as in 6 as in 6 | as in 6 | as in 6 | isostearic acids 10% pantothenyl alcohol 1% | 18 | 1.05 |
| 9 | as in 6 | as in 6 as in 6 | as in 6 | as in 6 | laevulinic acid 10% pantothenyl alcohol 1% | 11 | 0.3 |
| 10 | as in 6 | as in 6 as in 6 | as in 6 | as in 6 | undecenoic acid 10% pantothenyl alcohol 1% | 18 | 1.0 |
| 11 | as in 6 | neutral PA 69% | as in 6 | as in 6 | pantothenyl alcohol 1% | 18 | 0.7 |

Tab. 1 Galanthamine release from different galanthamine TTS Examples 6–8 and 10–11 prove that galanthamine penetrates through mice skin in a sufficient amount in vitro. The penetration rate may be increased by factor 1.5 by the additon of octanoic, undecenoic, oleic and isostearic acid.

The in-vitro-release was determined in a shaking water bath at 37° C. The acceptor medium was 100 ml physiological saline which was completely changed after 2, 4 and 8 hours. The concentration was determined by HPLC after 2, 4, and 8 and 24 hours. The penetration through mice skin was measured by means of Franz' diffusion cells.

Significations in the Table:
acidic polyacrylate (PA): acrylate copolymer of 2-ethyl-hexyl-acrylate, vinyl acetate, and acrylic acid with acid value 40.
neutral PA: acrylate copolymer of 2-ethyl hexyl-acrylate, vinyl acetate, and acrylic acid with acid value about 1.
polymethacrylate: copolymer with basic character, based on dimethylamino methacrylate and neutral methacrylic esters (KOH-value 180).

We claim:

1. A transdermal therapeutic system (TTS) for the administration of galanthamine to the skin said system having a backing layer which is impermeable to active substances and a pressure sensitive adhesive reservoir layer, characterized in that the reservoir layer comprises 40–80%-wt. polymer material selected from the group consisting of polyacrylates, 0.1–30% wt. plasticizers, and 0.1–30%-wt. galanthamine base or one of the pharmaceutically acceptable salts thereof.

2. The TTS according to claim 1 characterized in that the pressure sensitive adhesive layer comprises 0.1–30%-wt. penetration enhancers.

3. The TTS according to claim 2 characterized in that the penetration enhancer is a carboxylic acid.

4. The TTS according to claim 1 characterized in that the polymer material selected from the group consisting of polyacrylates is a polymerization product of acrylic acid and the esters thereof or of methacrylic acid and the esters thereof.

5. The TTS according to claim 4 characterized in that the esters of acrylic acid comprise as alcohol components straight-chain or branched alcohols having 4–10 carbons.

6. The TTS according to claim 4 characterized in that the esters of acrylic acid comprise as alcohol components alcohols having 2–4 carbons.

7. The TTS according to claim 4 characterized in that the esters of methacrylic acid comprise amino alcohols as alcohol components.

8. The TTS according to claim 4 characterized in that the polymer material comprises self-crosslinking or non-self-crosslinking acrylate copolymers.

9. The TTS according to claim 1 characterized in that the system is provided with a removable protective layer.

* * * * *